(12) United States Patent
Mazzoleni

(10) Patent No.: US 9,921,142 B2
(45) Date of Patent: Mar. 20, 2018

(54) PORTABLE HYDRAULIC BRINELL TESTING APPARATUS

(71) Applicant: Giancarlo Mazzoleni, Philadelphia, PA (US)

(72) Inventor: Giancarlo Mazzoleni, Philadelphia, PA (US)

( * ) Notice: Subject to any disclaimer, the term of this patent is extended or adjusted under 35 U.S.C. 154(b) by 157 days.

(21) Appl. No.: 15/044,506

(22) Filed: Feb. 16, 2016

(65) Prior Publication Data
US 2016/0245734 A1    Aug. 25, 2016

Related U.S. Application Data

(60) Provisional application No. 62/118,491, filed on Feb. 20, 2015.

(51) Int. Cl.
*G01N 3/42* (2006.01)

(52) U.S. Cl.
CPC ....... *G01N 3/42* (2013.01); *G01N 2203/0048* (2013.01); *G01N 2203/0098* (2013.01)

(58) Field of Classification Search
CPC ............... G01N 2203/0048; G01N 2203/0098
See application file for complete search history.

(56) References Cited

U.S. PATENT DOCUMENTS

| | | | | |
|---|---|---|---|---|
| 1,746,891 A * | 2/1930 | Gogan | ..... | G01N 3/42 73/83 |
| 2,009,316 A * | 7/1935 | Gogan | ..... | G01N 3/42 60/328 |
| 2,365,348 A * | 12/1944 | Lyon | ..... | G01N 3/42 417/464 |
| 2,498,136 A * | 2/1950 | Rupley | ..... | G01N 3/42 200/81.4 |
| 2,912,105 A * | 11/1959 | Allured | ..... | G01N 3/42 209/559 |
| 3,129,582 A * | 4/1964 | Borgersen | ..... | G01N 3/42 73/81 |
| 3,295,363 A * | 1/1967 | Delporte | ..... | G01N 3/42 73/81 |
| 3,478,568 A * | 11/1969 | Borgersen | ..... | G01N 3/42 254/93 R |
| 3,754,436 A * | 8/1973 | Saxton | ..... | G01N 3/42 356/626 |
| 4,245,496 A * | 1/1981 | Napetschnig | ..... | G01N 3/44 73/83 |
| 4,331,026 A * | 5/1982 | Howard | ..... | G01N 3/42 340/680 |
| 5,305,633 A * | 4/1994 | Weissenbacher | ..... | G01N 3/42 73/82 |

OTHER PUBLICATIONS

SUN hydraulics, Pilot operated, balanced piston sequence valve, Model FSFC, 2017.*

* cited by examiner

*Primary Examiner* — John Fitzgerald
(74) *Attorney, Agent, or Firm* — William B. Ritchie

(57) ABSTRACT

A portable testing apparatus for a Brinell test meeting the load time requirements of the ASTM E10 standard. The apparatus incorporates a hydraulic accumulator acting on a cylinder which is connected to an indenter. The accumulator keeps a constant force on the indenter for the period of time of the test despite hydraulic leakage or creep of the indenter into the material that would cause a reduction in pressure if not for the accumulator. Usually, the test time length is 10 seconds. Pressure is set using springs usually in a settable sequence valve.

19 Claims, 2 Drawing Sheets

PORTABLE HYDRAULIC BRINELL TESTING APPARATUS

This application claims benefit of U.S. Provisional Application Ser. No. 62/118,491, filed Feb. 20, 2015, pursuant to 35 USC § 119(e).

FIELD OF THE INVENTION

This invention relates to hardness testing equipment, in particular, portable testing equipment for a Brinell test meeting ASTM E10 standard.

BACKGROUND OF THE INVENTION

The Brinell scale characterizes the indentation hardness of materials through a scale of penetration of an indenter loaded on a material test-piece. According to the American Society of Testing and Materials (ASTM) E10 Standard, the Brinell test requires the application to an indenter of 10 mm in diameter of a determined test force (load), usually 500 Kgf for Aluminum and 3000 Kgf for Steel, for a specified amount of time, 10 to 15 seconds.

Current portable Brinell Testers as disclosed in U.S. Patent Application Publication No. 2014/0230529, published Aug. 21, 2014, which is based on its predecessor U.S. Pat. No. 3,129,582, employs a hydraulic cylinder activated by a hand pump with a release valve when a certain pressure is reached; therefore, a certain resulting load is achieved. The problem with this approach is that the load is only applied instantaneously and it does not remain applied for the specified time. Therefore, the test does not meet the ASTM E10 specification but an ad-hoc specification; that is, E110 created just for this instrument.

Some users can test according to this specification but the majority must meet the full E10 specification. Thus, there is not found in the prior art a portable Brinell testing apparatus that meets the ASTM E10 standard.

SUMMARY OF THE INVENTION

It is an aspect of the invention to provide a portable hydraulic Brinell testing apparatus that meets ASTM E10 standard.

It is an aspect of the invention to provide a portable hydraulic Brinell testing apparatus that features an accumulator that keeps the pressure constant during the test period despite creep from the indenter moving in the test piece and hydraulic leakage.

It is still another aspect of the invention to provide a portable hydraulic Brinell testing apparatus that can be made costing substantively the same as prior art portable Brinell testing apparatus.

Finally, it is an aspect of the invention to provide a portable hydraulic Brinell testing apparatus that can be made from readily available components or incorporated in a self-contained module.

DETAILED DESCRIPTION OF THE INVENTION

Figure 1:
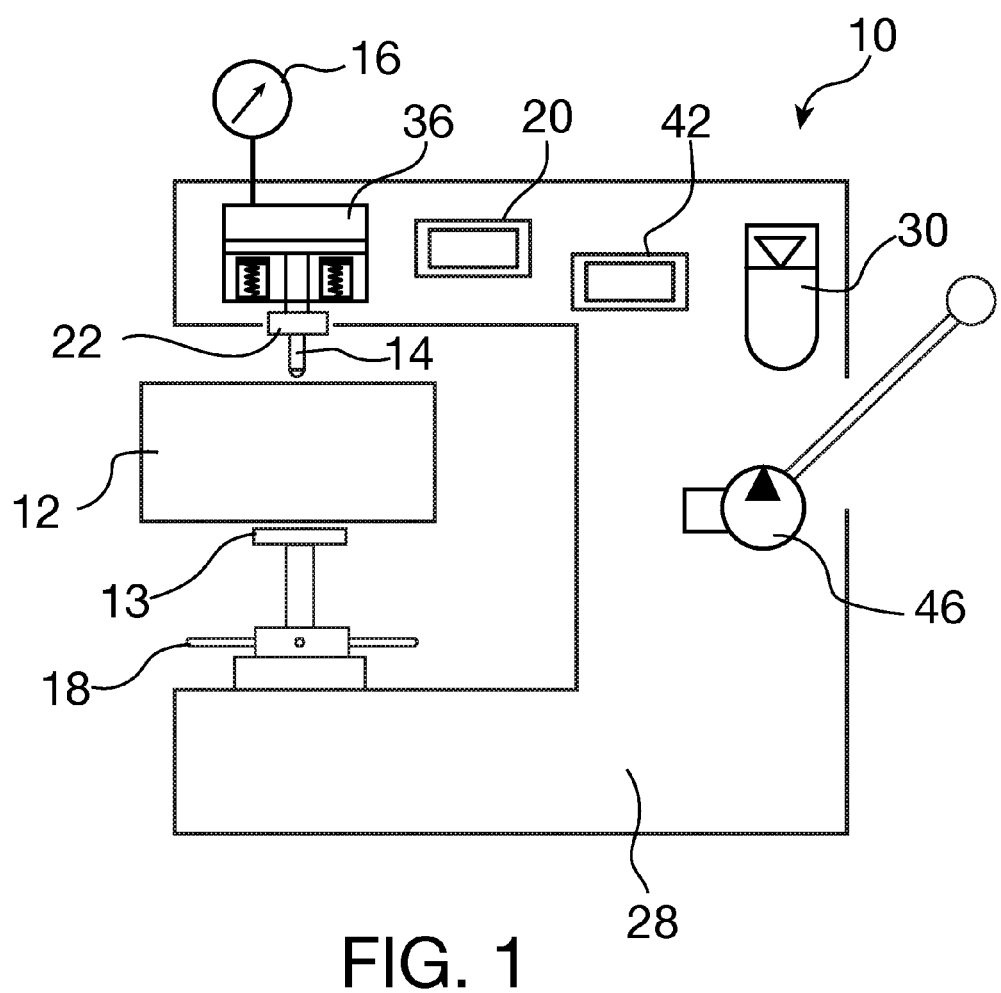
FIG. 1 is a schematic of the portable hydraulic Brinell hardness testing apparatus in accordance with the invention.
Figure 2:
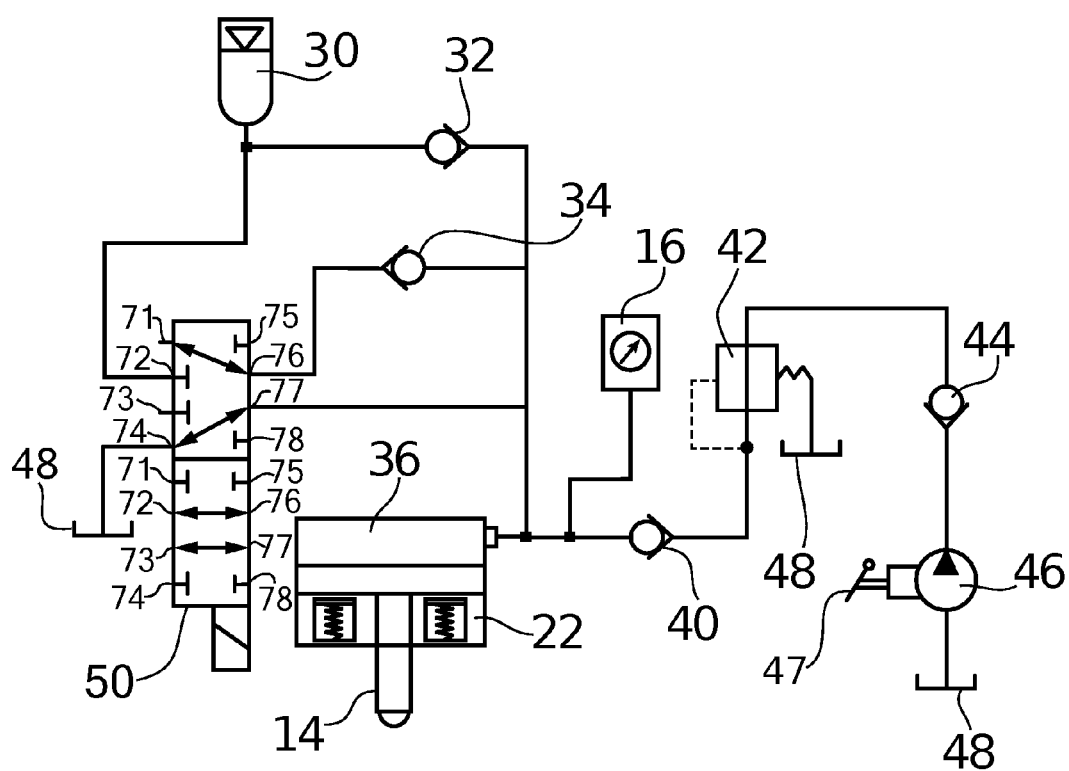
FIG. 2 is a schematic of the hydraulic system of the portable hydraulic Brinell testing apparatus in accordance with the invention showing the invention at rest.

Referring now to FIGS. 1 and 2, portable instrument 10 described herein solves the problem of prior art portable systems meeting ASTM E10 standards. This is accomplished by incorporating hydraulic accumulator 30 acting on single spring return cylinder 36 (such as made by ENERPAC of Columbus, Wis., Model RSM-50) through precision sequence valve 42 (such as made by SUN HYDRAULICS of Sarasota, Fla., Model RSFCLAN).

Hydraulic accumulator 30 is preferably a miniature accumulator (such as made by HAWE HYDRAULIC of Charlotte, N.C., Model Type AC 0725/1A). Accumulator 30 helps compensate for the loss of force due to indenter 14 creep and hydraulic leakage.

As shown in FIG. 1, invention 10 is activated by handle 47 which controls hydraulic pump 46 (made by HAWE HYDRAULICS, Model HE13 A-K0.5 100). Pump 46 is preferably a double acting pump instead of a single acting pump in order to constantly maintain hydraulic pressure and therefore, provides constant force to indenter 14.

Invention 10 uses accumulator 30 to maintain the test force (load) and sustains that force for the required time for test, usually at least 10 seconds. The output of sequence valve 42 is fed to both the top of cylinder 36 and to holding accumulator 30. The bottom of cylinder 36 is connected to the indenter holder 22.

The prior art devices use a simple spring poppet in order to minimize loss of hydraulic pressure and thus, force, but it is not as efficient as sequence valve 42. Cylinder 36 that applies the load can be directly in line with indenter 14 or acting on an advantage beam/lever (not shown) having a leverage of 5 to 1 or 10 to 1; thus, lowering the pressure and load required in the hydraulics but requiring more fluid flow.

In operation, invention 10 works as follow:

Test piece 12 is placed onto anvil 13 of tester 10 specifically on elevating screw assembly 18 which is a jack screw well known in the art. Test piece 12 is raised until test piece 12 contacts indenter 14 and closes the gap between indenter holder 22 and a loading beam (not shown) or directly onto cylinder 36.

At this point, the pressure is allowed to build up in the system by shifting the loading/unloading valve 50 which is a two position selector valve (such as made by BRAND HYDRAULICS of Omaha, Nebr., Model DS08BK) from the rest position (shown in FIG. 2 with the arrows crissed-crossed) to the testing position (not shown, arrows straight across). This connects accumulator 30 (previously going to blocked port 71) from port 72 to port 76 through valve 34 to the top of cylinder 36. At the same time, port 74 (previously connecting cylinder 36 through port 77 to tank 48) is blocked and the top of cylinder 36 through port 77 now goes to blocked port 73 so allowing pressure to build into cylinder 36.

Pump 46 is activated to provide the proper pressure until pressure gauge 16 (made by ENERPAC, Model GP-10S) reaches the predetermined value.

At that point, pump 46 can be stopped. Sequence valve 42 allows downstream flow only. The amount of pressure is set by internal spring of sequence valve 42 with any excess pressure being diverted to tank 48. Pressure in sequence valve 42 could also be set by a stack of belleville springs that provide a flatter spring rate profile as compared to regular coiled springs therefore assuring smoother transition from close to open to close. Still another option is the use of two nested concentric springs, the outer one providing the majority of the force needed, while the inner one permits fine adjustment of the relief pressure.

The same pressure is fed to holding accumulator 30, therefore accumulator 30 has enough pressure to compensate for the minimal drop in pressure caused by the creep of indenter 14 into the material during the holding time of the test. After the specified time (min 10 sec.) the loading/unloading valve 50 is returned to the rest position, blocking the pressure from the holding accumulator 30 and, by connecting the cylinder 36 to tank 48 allowing the spring in cylinder 36 to retract indenter 14 so that test piece 12 can be removed.

Check valve 40 allows flow from sequence valve 42 and prevents backpressure into it; check valve 32 allows flow into accumulator 30 and prevents back flow in that part of the circuit; check valve 34 allows flow from accumulator 30 to cylinder 36 and prevents back flow in that part of the circuit. Note that all check valves are the same (such as made by HAWE HYDRAULICS, Model RK0/RB0).

The force can be calibrated by adjusting the spring in precision sequence valve 42. This calibration only has to be done at the time of manufacture. Verification or re-calibration is necessary periodically, such as every 12 months or so.

With the addition of a button load cell or pressure transducer (such as made by Forsentek of Shenzhen, China, Model No. FC50 (5000 Kg capacity)) in combination with a sensor Load Cell Amplifier Model LAU 63.1 (such as made by Sensor Techniques of Cowbridge, UK) connected to readout display 20 (such as provided by SENECA DISPLAY of Padova, Italy, Model S311AK) and powered by a battery pack (such as Model No. CU-J970 made by AA PORTABLE POWER PAC of Richmond, Calif.), a user can then read the actual load being applied.

The use of hydraulic hand-operated pump 46 can be replaced or augmented by a 12 V electric pump (not shown) as another way to generate the pressure in addition to or instead of hand pump 46. This electric pump is preferably of the type made by Bucher Hydraulics of Klettgau-Griessen, Germany, Model C117PE/V0-R106-E56-AP05/** S819. This electric pump would be powered by a battery pack well known in the art.

While this invention has been described for use with a portable system, the invention could also be used with a bench Brinell tester that is firmly fixed in a location.

Although the present invention has been described with reference to certain preferred embodiments thereof, other versions are readily apparent to those of ordinary skill in the preferred embodiments contained herein.

What is claimed is:

1. A hydraulic Brinell testing apparatus for measuring the hardness of a test material positioned in said apparatus between an indenter connected to the bottom of a cylinder and an anvil wherein said apparatus having pumpable hydraulic fluid for holding a specified pressure of the hydraulic fluid for a specified period of time in order to meet the load time requirements of the ASTM E10 standard, such that said apparatus comprises:
   a pump for pumping the hydraulic fluid to the specified pressure;
   a sequence valve having an hydraulic output and connected between said pump and the cylinder, wherein said sequence valve having a settable pressure of the hydraulic fluid that said pump provides;
   a hydraulic accumulator also connected to the output of the sequence valve such that said accumulator maintains the settable pressure in the cylinder against the indenter thus maintaining the test force for the required period of time despite any drop in pressure in the cylinder caused by the creep of the indenter into the test material and hydraulic leakage during the time period of the test, thus meeting the load time requirements of the ASTM E10 standard.

2. The hydraulic Brinell testing apparatus of claim 1 further comprising:
   a hydraulic fluid storage tank connected to said sequence valve for storing hydraulic fluid;
   a loading/unloading valve having a plurality of selectable ports for controlling the flow of the hydraulic fluid to and from said hydraulic accumulator; and to and from the cylinder and said tank.

3. The hydraulic Brinell testing apparatus of claim 2 wherein said loading/unloading valve is a molded one-piece manifold.

4. The hydraulic Brinell testing apparatus of claim 2 wherein said loading/unloading valve is a self-contained two position selector valve.

5. The hydraulic Brinell testing apparatus of claim 2 wherein said loading/unloading valve is made of separate individual valves working to open or block passages to the cylinder, said tank and said hydraulic accumulator.

6. The hydraulic Brinell testing apparatus of claim 2 wherein said sequence valve has the pressure set by means of a single spring.

7. The hydraulic Brinell testing apparatus of claim 2 wherein said sequence valve has the pressure set by means of a stack of belleville springs that provide a flatter spring rate profile as compared to regular coiled springs therefore assuring smoother transition from close to open to close.

8. The hydraulic Brinell testing apparatus of claim 2 wherein said sequence valve has the pressure set by means of two nested concentric springs, the outer one providing the majority of the force needed, while the inner one permits fine adjustment of the relief pressure.

9. The hydraulic Brinell testing apparatus of claim 2 further comprising a first and a second check valves before and after said sequence valve, respectively, to minimize the loss of hydraulic pressure thus, the force that is being applied to the indenter.

10. The hydraulic Brinell testing apparatus of claim 2 wherein said pump is a single acting manual pump.

11. The hydraulic Brinell testing apparatus of claim 2 wherein said pump is a double acting manual pump.

12. The hydraulic Brinell testing apparatus of claim 2 further comprising an indicator that indicates when the desired pressure has been reached by said pump.

13. The hydraulic Brinell testing apparatus of claim 2 further comprising a first check valve between the pump and said sequence valve to minimize the loss of hydraulic pressure, thus the force that is being applied to the indenter.

14. The hydraulic Brinell testing apparatus of claim 13 further comprising a second check valve between the cylinder and said sequence valve to minimize the loss of hydraulic pressure thus, the force that is being applied to the indenter.

15. The hydraulic Brinell testing apparatus of claim 2 wherein said pump is an electrical powered pump.

16. The hydraulic Brinell testing apparatus of claim 15 wherein said indicator is a pressure gauge.

17. The hydraulic Brinell testing apparatus of claim 15 further comprising a load cell and an electronic display associated with said indicator to provide a continuous readout of the force being applied to the test material being measured such that the shifting of said sequence valve can be set above the value of the pressure required to reach the predetermined force preventing said sequence valve from shifting thus eliminating leakage from said sequence valve since pump can stop pumping when the predetermined force is reached.

18. The hydraulic Brinell testing apparatus of claim 15 further comprising a pressure transducer associated with an electronic display with said indicator to a continuous readout of the force being applied to the test material being measured such that the shifting of said sequence valve can be set above the value of the pressure required to reach the predetermined force preventing said sequence valve from shifting thus eliminating leakage from said sequence valve since pump can stop pumping when the predetermined force is reached.

19. A hydraulic Brinell testing apparatus for measuring the hardness of a test material positioned in said apparatus between an indenter and an anvil such that said indenter is pushed into said test material wherein said apparatus comprises:
- a hydraulic accumulator such that said hydraulic accumulator maintains a settable pressure in the indenter thus maintaining the test force for the required period of time despite any drop in pressure caused by the creep of the indenter into the test material and hydraulic leakage during the time period of the test, thus holding the load time requirements of the ASTM standard.

* * * * *